United States Patent
Mark et al.

(10) Patent No.: US 10,398,458 B2
(45) Date of Patent: Sep. 3, 2019

(54) MICROSURGICAL INSTRUMENTS

(71) Applicant: Nico Corporation, Indianapolis, IN (US)

(72) Inventors: Joseph L. Mark, Indianapolis, IN (US); Brian C. Dougherty, Terre Haute, IN (US)

(73) Assignee: Nico Corporation, Indianapolis, IN (US)

( * ) Notice: Subject to any disclaimer, the term of this patent is extended or adjusted under 35 U.S.C. 154(b) by 1076 days.

(21) Appl. No.: 14/215,284

(22) Filed: Mar. 17, 2014

(65) Prior Publication Data

US 2014/0277046 A1 Sep. 18, 2014

Related U.S. Application Data

(60) Provisional application No. 61/790,679, filed on Mar. 15, 2013.

(51) Int. Cl.
*A61B 17/29* (2006.01)
*A61B 17/3201* (2006.01)
*A61B 17/30* (2006.01)

(52) U.S. Cl.
CPC .......... *A61B 17/29* (2013.01); *A61B 17/3201* (2013.01); *A61B 2017/2923* (2013.01); *A61B 2017/2929* (2013.01); *A61B 2017/305* (2013.01)

(58) Field of Classification Search
CPC ..... A61B 17/29; A61B 17/32; A61B 17/3201; A61B 2017/2923; A61B 2017/2929; A61B 2017/305; A61B 17/2841; A61B 2017/4845; A61B 2017/2912; A61B 17/320016; A61B 17/32053; A61B 17/34; A61B 10/04; A61B 10/0283; A61B 10/0275; A61B 10/0026; A61B 10/0233; A61B 2010/0208; A61B 2017/405
USPC ....................................................... 606/170
See application file for complete search history.

(56) References Cited

U.S. PATENT DOCUMENTS

| | | | |
|---|---|---|---|
| 5,304,190 A | | 4/1994 | Reckelhoff et al. |
| 5,366,476 A | * | 11/1994 | Noda ................. A61B 17/2909 606/206 |
| 5,575,799 A | | 11/1996 | Bolanos et al. |
| 6,090,120 A | * | 7/2000 | Wright ........... A61B 17/320068 606/1 |
| 7,588,176 B2 | | 9/2009 | Timm et al. |
| 2003/0060732 A1 | * | 3/2003 | Jacobsen ............... A61M 25/09 600/585 |
| 2012/0074200 A1 | | 3/2012 | Schmid et al. |

* cited by examiner

*Primary Examiner* — George J Ulsh
(74) *Attorney, Agent, or Firm* — Kristin L. Murphy; Honigman LLP (57) ABSTRACT

A surgical instrument is disclosed herein. The surgical instrument comprises a housing, a first actuation member, a second actuation member, and a first cannula. The first actuation member is configured for imparting a reciprocating action to a portion of the instrument. The second actuation member configured for imparting a rotational action to a portion of the instrument. The first cannula is operatively connected to the second actuation member, such that the first cannula is configured for rotational movement with respect to the housing. In one arrangement, a wire member is disposed within the first cannula and is configured to rotate with the first cannula.

16 Claims, 9 Drawing Sheets

MICROSURGICAL INSTRUMENTS

CROSS-REFERENCE TO RELATED APPLICATIONS

This claims the benefit of U.S. provisional application Ser. No. 61/790,679 filed Mar. 15, 2013, the disclosure of which is hereby incorporated in its entirety by reference herein.

TECHNICAL FIELD

The present disclosure relates to surgical instruments that may be used for microsurgical procedures.

BACKGROUND

Microsurgery is a surgical technique for operating on minute structures which require magnification to see the detail of the anatomy, with specialized, miniaturized precision instruments. Microsurgery permits operations that were once virtually impossible, including, for example, removal of tumors intricately involved with vital eloquent structures of the brain. These types of procedures require safely lifting certain critical structures to move or hold them during a procedure without damaging them or incurring trauma to them. Due to the delicate nature of the structures involved, the design of suitable surgical instruments for these types of procedures presents certain challenges.

For example, because the need to create a narrow and often deep surgical corridor to access the structures being subject to the operation are in the same focal surgical site and often difficult to differentiate the normal from the abnormal tissue, many known surgical device have line of sight issues whereby the effective end of the instrument is very difficult to observe during a procedure without also occluding the surgeons view of the surgical site. As a result, users are often required to hold the instrument at awkward angles so as to maintain visibility during the procedure, which may lead to unintended movements by the operator causing harm to normal tissues. Often because of the size and angle at which the instrument must be entered into the surgical site, the actual use of the instrument blocks the surgeons view of the surgical site during its use and the surgeon effectively uses the instrument "blindly" and removes the instrument from the surgical field so as to inspect the outcome of the use of the instrument. If unsatisfactory, then the instrument is then placed again in the surgical field for additional work. This can often go on for multiple passes the surgical site. Such repeated action can cause damage to the tissues which line the surgical corridor due to the bumping of the instrument as they are passed in and out, as well as increased surgeon fatigue issues.

Manipulation of the microsurgical device is also difficult within the surgical field. For example, while a device may be configured to cut tissue or grasp different structures, often there is no mechanism to change angles of orientation of the effector end of the device during the cutting or grasping operation while it is in use within the surgical site. Accordingly, the user has traditionally been required to extract the device from the surgical field to reposition the device for further operation or remove the device and request that a different angled device be provided. This action thus lengthens a procedure. Moreover, depending on the set up in the operating suite, in some instances the repositioned angle requires the user to hold and operate the device in an awkward manner, also leading to fatigue and surgical errors.

Based on the foregoing, an improved device that allows for easy manipulation for both line of sight issues, as well as to permit flexibility of use during a procedure.

BRIEF DESCRIPTION OF THE DRAWINGS

Exemplary embodiments of the present disclosure will now be described in greater detail with reference to the attached figures, in which.

DETAILED DESCRIPTION

Referring now to the discussion that follows and also to the drawings, illustrative approaches to the disclosed instruments and methods are shown in detail. Although the drawings represent some possible approaches, the drawings are not necessarily to scale and certain features may be exaggerated, removed, or partially sectioned to better illustrate and explain the present disclosure. Further, the descriptions set forth herein are not intended to be exhaustive or otherwise limit or restrict the claims to the precise forms and configurations shown in the drawings and disclosed in the following detailed description.

Described herein are microsurgical instruments that are configured for microsurgical operations, such as vascular procedures. The microsurgical instruments are particularly suited for minimally invasive surgical procedures that are performed through a port, such as that which is disclosed in U.S. patent application Ser. No. 13/280,015, the contents of which are incorporated in its entirety.

Figure 1:
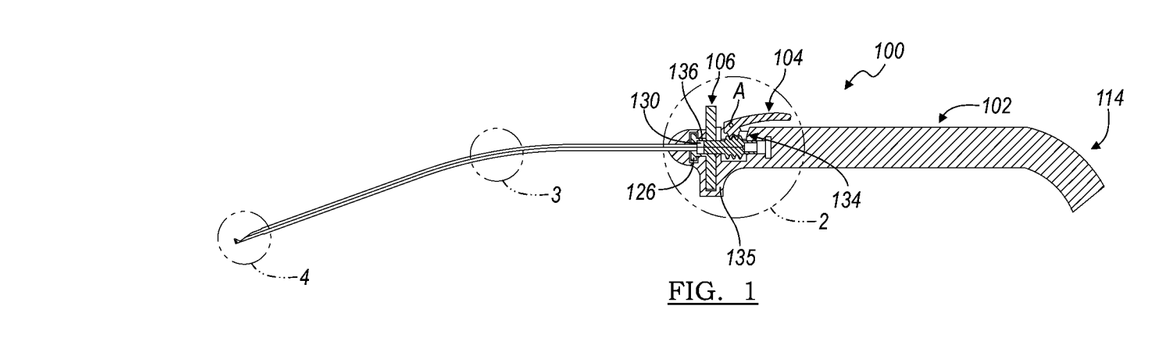
FIG. 1 is a cross-sectional view of a first exemplary embodiment of a microsurgical instrument.

Referring to FIG. 1, a first exemplary configuration of a microsurgical instrument 100 will be described. Microsurgical instrument 100 comprises a handpiece, 102, a first actuation mechanism 104, a second actuation mechanism 106, an inner cannula 108 (best seen in FIGS. 3-5), an outer cannula 110, and a center wire 112. The handpiece 102 may be generally elongate, as shown in FIG. 1. A proximal end 114 may curve downwardly to define a grip section.

Figure 2:
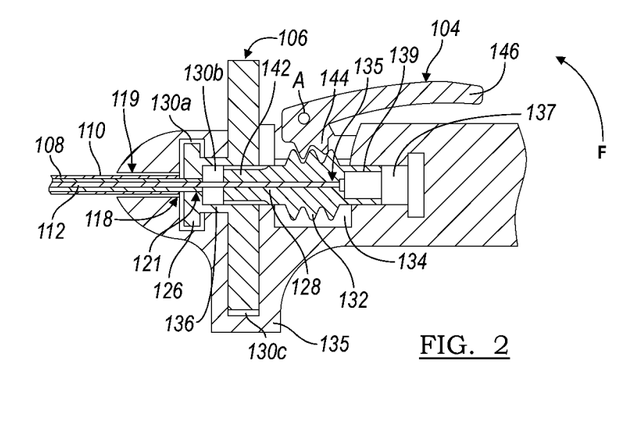
FIG. 2 is an enlarged view of area 2 taken from FIG. 1.

The outer cannula 110 is defined by a distal end 116 and a proximal end 118 (best seen in FIG. 2). The proximal end 118 is non-rotatably fixed within a channel of the handpiece 102. In one exemplary configuration, the channel 119 extends from a distal end of the handpiece 102 to a cavity 130 formed in the handpiece 102.

In one exemplary configuration, outer cannula 110 includes an offset bend (as illustrated in FIG. 1). The offset bend allows for a clear line of sight during the procedure which is useful for delicate procedures. In another exemplary configuration, the outer cannula 110 may be constructed of a suitable material that is selectively malleable such that the outer cannula 110 may be bent to a desired location, but once bent will maintain its position.

Figure 4:
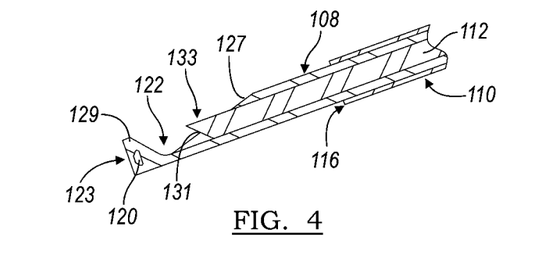
FIG. 4 is a perspective view of area 3 taken from FIG. 1.
Figure 5:
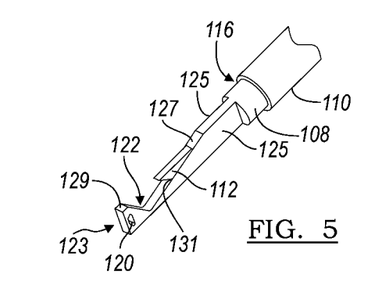
FIG. 5 is an enlarged perspective view of area 4 taken from FIG. 1.

The inner cannula 108 is received within the outer cannula 110. The inner cannula 108 is fixed to the second actuation member 106. For example, a proximal end 121 of the inner cannula may be operatively fixed to the second actuation member 106. In one exemplary configuration, the second actuation member 106 is configured as a rotation wheel. Thus, when rotation wheel 106 is rotated, inner cannula 108 will also rotate. A distal end 123 of the inner cannula 108 may include a key way 120, as best seen in FIG. 4. In one exemplary arrangement, key way 120 is configured to receive a suitable material that has sufficient rigidity to receive an opposing cutting blade material without dulling a blade (as will be explained in further detail below). Some examples of suitable material include, but are not limited to, an epoxy resin or thermoplastic resin. In one exemplary configuration, the key way 120 may be insert molded with a resin to form a cut block at the distal end of inner cannula 108.

Inner cannula 108 also defines an opening 122 that is positioned adjacent the distal end 123, as will be discussed in further detail below. The inner cannula 108 may include one or more relief cut-outs 124 (best shown in FIG. 3) to allow for flexibility of the inner cannula 108 while still providing for columnar strength. The distal end 123 of the inner cannula 108 may be configured with a reduced profile for ease of manipulation in narrow surgical corridors, as well as providing increase field of vision. In one exemplary configuration, the distal end 123 is defined by generally opposing planar lateral surfaces 125 that are positioned inboard of an outer periphery of the inner cannula 108, on a portion of the inner cannula 108 that protrudes from outer cannula 110. The reduced profile section further includes an inclined portion 127 that includes the opening 122. The distal end 123 of the inner cannula 108 includes a toe portion 129 that serves as a cut block, as will be explained in further detail below.

The center wire 112 is positioned within the inner cannula 108. While not specifically shown, the center wire 112 may also include one or more relief cut-outs, similar to cut-outs 124 for the inner cannula 108, to allow for flexibility while providing columnar strength. The center wire 112 includes a cutting edge 131 on a distal end 133 thereof. A proximal end 135 of the center wire 112 is fixed to a coupling member 128 (best shown in FIG. 2). Coupling member 128 includes a gear mechanism 132 attached thereto. The coupling member 128 is partially disposed in the cavity 130 of the handpiece 102. The gear mechanism 132 is disposed within a slot 134 that is in communication with the cavity 130. The slot 134 opens through part of the handpiece 102, as will be discussed in further detail below.

The cavity 130 formed within the handpiece 102 includes several sections. A first section 130a is configured to receive hub member 126, such that once hub member 126 is disposed within the first section 130a, hub member 126 may not be easily removed from handpiece 102. In one exemplary arrangement, at least a portion of the handpiece is separable from a remaining portion, such that the hub member 126 may be positioned within the first section 130a. Once positioned, the handpiece is assembled and fixedly secured together to trap the hub member 126 within the first section 130a. In another exemplary arrangement, the hub member 126 may be made of a compliant material having some memory that may be selectively deformed as hub member 126 is press-fit into the first portion 130a. Once the hub member 126 enters the portion 130a of the cavity, the hub member 126 will return to its original shape, thereby being trapped within the first portion 130a.

Cavity 130 further includes a second portion 130b and a second portion 103c. Second portion 130b joins first portion 103a and third portion 130c. Third portion 130c is sized to receive rotation wheel 106 and is thus larger than second portion 130b. Third portion 130c extends into an extension member 135 that extends outwardly from an outer periphery of handpiece 102.

Figure 6:
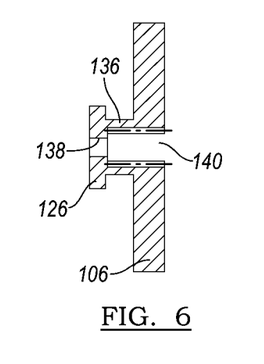
FIG. 6 is an enlarged cross-sectional view of an actuation mechanism.

Rotation wheel 106 is mounted to hub member 126 by a web 136. Details of the hub member 126 may be best seen in FIG. 6. The hub member 126 is positioned within the first cavity portion 130a of handpiece 102. A channel 138 extends through the hub member 126 and opens into a cavity 140 formed by the web 136 and rotation wheel 106. The inner cannula 108 is fixed within the channel 138 of the hub member 126 such that the inner cannula 108 rotates with the rotation wheel 106. A distal end 142 of coupling member 128 is received within the cavity 140. In one exemplary arrangement, the coupling member 128 is configured to selectively slide within the cavity 140, relative to the rotation wheel 106, as will be explained in further detail below.

Hub member 126, rotation wheel 106 and coupling member 128 are positioned within cavity 130 formed within a distal portion of handle 102, as best shown in FIG. 2. A portion of rotation wheel 106 extends outwardly from a portion of the handpiece 102. A remaining portion of the rotation wheel 106 is disposed within the third portion of the cavity 130c. First actuation member 104 is operatively engaged to gear mechanism 132.

More specifically, in one exemplary arrangement, the first actuation member 104 is configured as a lever and includes teeth members 142 disposed on a distal end 144 that are configured to operatively engage gear 132 formed on the coupling member 128. The teeth members 142 extend through an opening of the handpiece 102 that is in communication with slot 134. The gear 132 of the coupling member 128 is disposed within the slot 143.

A depression 137 extends proximally from the slot 143 within the handpiece 102. The depression 137 is configured to receive an extension member 139 of the coupling member 128. More specifically, the extension member 139 is disposed proximally of the gear 132 and is configured to be at least partially disposed within the depression 137 to maintain the coupling member 128 within the slot 134 of the handpiece 102.

First actuation member 104 is pivotally attached to a portion of handle 102 such that it is adjacent to rotation wheel 106. In one exemplary configuration, a torsional spring (not shown) may be engaged at a pivot point A to bias first actuation member 104 into a ready position, namely a position whereby a proximal end 146 of the first actuation member 104 biased upwardly from an outer surface of handpiece 102. Alternatively, a coil spring (not shown) may be disposed within the cavity 130 to bias the first actuation member 104. When the first actuation member 104 is activated against a biasing force F created by the spring, center wire 112 may be advanced forward to traverse the opening 122 in the inner cannula 108. More specifically, actuation of the first actuation member 104 will cause coupling member 128 to slide forward within the cavity 140 formed by the web 136 and rotation wheel 106. Because a proximal end of the center wire 112 is fixedly connected to the coupling member 128, as the coupling member 128 moves, center wire 112 will also move.

Further, to maintain the orientation of the cutting edge 131 of the center wire 112 with respect to the inner cannula 108, the distal end 142 of the coupling member 128 and the rotation wheel 106 maybe operatively connected together with a splined connection. In another exemplary arrangement, the distal end 142 may be a hexagonal cross-section that cooperates with a mating hexagonal opening formed through the rotation wheel 106. Other cross-sectional shapes with corresponding mating openings are also contemplated. With this configuration, center wire 112 is rotationally fixed with the rotation wheel 106 such that as rotation wheel 106 rotates, center wire 112 will also rotate. However, the splined or other mated connection will enable center wire 112 is slide axially independent of the rotation wheel 106.

As the first actuation member 104 is depressed, the center wire 112 traverses the opening 122. Any tissue or vessels that are positioned within the opening 122 as center wire 112 is traversed across will be cut. A full depression of the first actuation member 104 will cause the cutting edge 131 to engage against the cut block. However, because the cut block is constructed out of material that is compliant, such engagement will not serve to damage the cutting edge 131. Continued depression of first actuation member 104 will maintain the cutting edge 131 center wire 112 against the cut block. This action may be desired when withdrawing the instrument 100 from a surgical site so as not to unintentionally rake the opening 122 against tissue. It may also be desirable to have the cutting edge 131 in engagement with the cut block when rotation of the distal end 123 of the inner cannula 108 is desired.

Because the first actuation mechanism 104 is positioned adjacent the second actuation mechanism 106, a user can actuate the center wire 112 and rotate the inner cannula 108 using the same hand. For example, the user's hand may be wrapped around a portion of the handle 102 of the instrument 100, with a thumb engaging the proximal end 146 of the first actuation member 104. A finger of the same hand as the thumb may engage the second actuation member 106. By only requiring a single hand to achieve both axial movement of the center wire 112 and rotation of the inner cannula 108, easier manipulation of the instrument 100 may be achieved, without requiring the user to reposition his or her hand in awkward positions. This configuration also allows for reduced visibility concerns, as an optimal site line may be chosen by the user, without requiring the user to manually rotate the entire device to achieve a desired cutting operation. Further, because the first and second actuation members 104, 106 may be easily activated with a single hand, the second hand is free to handle other surgical instruments such as an aspirator or irrigation mechanism that may be needed in a surgical procedure.

Figures 7, 8, 9:
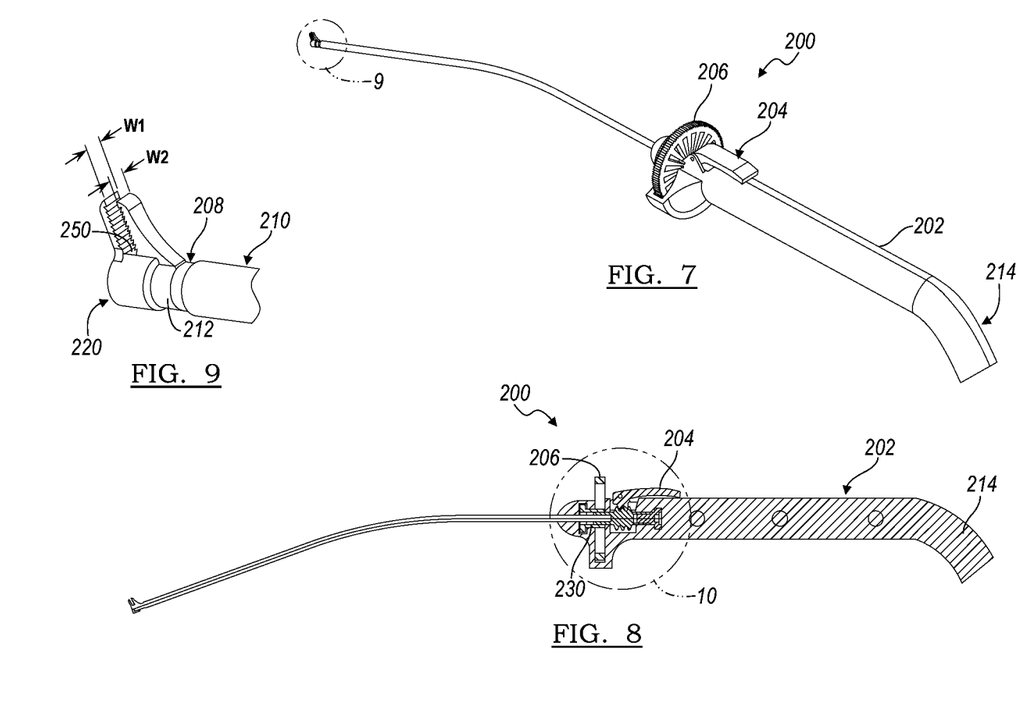
FIG. 7 is an elevational view of a second exemplary embodiment of a microsurgical instrument.
FIG. 8 is a cross-sectional view of the microsurgical instrument of FIG. 7.
FIG. 9 an enlarged perspective view of area 8 taken from FIG. 8.

Another exemplary embodiment is illustrated in FIGS. 7-11. Microsurgical instrument 200 is similar to microsurgical instrument 100. Microsurgical instrument 200 comprises a handpiece 202, a first actuation mechanism 204, a second actuation mechanism 206, an inner cannula 208, an outer cannula 210, and a center wire 212. The handpiece 202 may be generally elongate, as shown in FIG. 8. A proximal end 214 may curve downwardly to define a grip section.

Figure 10:
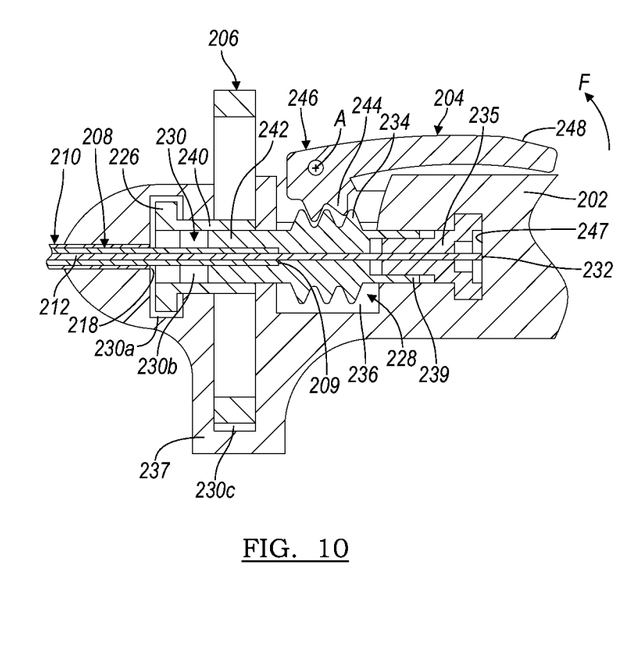
FIG. 10 is an enlarged cross-sectional view of area 10 of the microsurgical instrument of FIG. 8.

The outer cannula 210 is defined by a distal end 216 and a proximal end 218 (best seen in FIG. 10). The proximal end 218 is non-rotatably fixed within a channel of the handpiece 202, as shown in FIG. 10, similar to the configuration shown with respect to instrument 100. The channel may extend from a distal end of the handpiece 102 to a cavity 230 formed in the handpiece 102. In one exemplary configuration, outer cannula 210 includes an offset bend (as illustrated in FIGS. 7-8) that allows for a clear line of sight during the procedure. In another exemplary configuration, the outer cannula 210 is configured to be selectively malleable such that the outer cannula 210 may be bent to a desired configuration, but once bent will maintain its position.

The inner cannula 208 is received within the outer cannula 210. The inner cannula 208 includes a proximal end 209 that is operatively connected to the second actuation member 206. In one exemplary configuration, the second actuation member 206 is configured as a rotation wheel. Thus, when rotation wheel 206 is rotated, inner cannula 208 also rotates. In one exemplary arrangement, inner cannula 208 is fixed to a coupling mechanism 228 disposed within the handpiece 202, as will be described below in greater detail.

In one exemplary arrangement, at a distal end 219 of the inner cannula 208, an end cap portion 220 is mounted. End cap portion 220 fixedly carries a first jaw member 221. First jaw member 221 may further include a textured gripping surface 223 that is configured to grasp tissue or other structures. In one exemplary arrangement, gripping surface 223 is configured as a series of alternating grooves and ridges. However, it is understood that other textured surfaces are within the scope of this disclosure. In one exemplary configuration, end cap portion 220 further comprises a retaining mount 225. Retaining mount 225 is configured to receive center wire 212 therein such that a distal end 227 of center wire 212 is fixedly secured to the end cap portion 220. While not shown, a distal bottom edge of cap portion 220 may be rounded to eliminate any sharp corners that may damage tissue or other structures.

Figure 3:
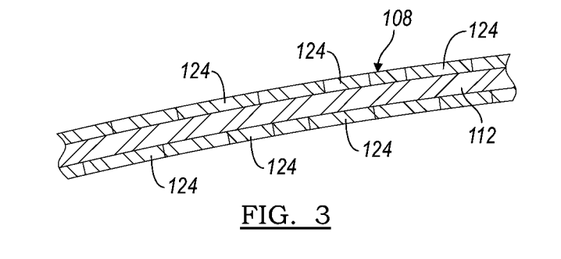
FIG. 3 is an enlarged view of area 3 taken from FIG. 1, with an outer cannula removed for clarity.

While not shown, inner cannula 208 may include one or more relief cut-outs similar to relief cut-outs depicted in FIG. 3 with respect to microsurgical instrument 100. The relief cut-outs allow for flexibility of the inner cannula 208, while providing for columnar strength, thereby permitting selective bending of the instrument 200 to a desired configuration.

Figure 11:
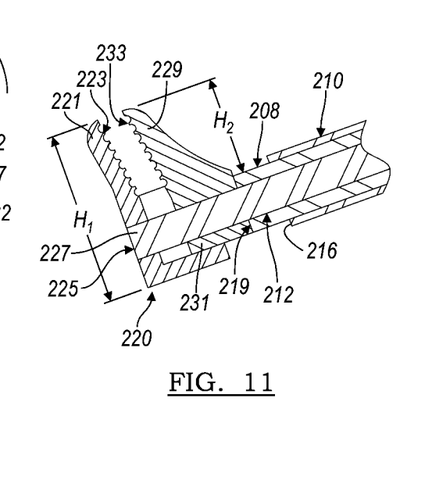
FIG. 11 is an enlarged cross-sectional view of area 10 taken from FIG. 8.

A second jaw member 229 is carried on a sleeve member 231. Sleeve member 231 is slidably disposed about center wire 212 and fixedly secured to the distal end 219 of the inner cannula 208. Thus, the second jaw member 229 is operatively connected to the inner cannula 208 such that the second jaw member 229 is rotationally fixed with respect to the inner cannula 208. Second jaw member 229 may be provided with a textured gripping surface 233 that is oriented in opposing relationship with gripping surface 223, as shown in FIG. 11.

In one exemplary arrangement, the profile of second jaw member 229 is sized to be smaller than the first jaw member 221 to provide increased visibility. For example, as best seen in FIG. 9, in one arrangement, first jaw member 221 may be provided with a width $W_1$ that may be sized to be wider than a width $W_2$ of second jaw member 229. In yet another exemplary arrangement, the first jaw member 221 may be provided with a height $H_1$ that is greater than a height $H_2$ of the second jaw member 229.

The center wire 212 is positioned within the inner cannula 208. Much like the arrangement of microsurgical instrument 100 depicted in FIG. 3, the center wire 212 may include one or more relief cut-outs to allow for flexibility while providing for columnar strength, similar to those shown with respect to relieve cut-outs 125 of inner cannula 108.

A proximal end 232 of the center wire 212 extends through coupling member 228. Coupling member 228 includes a gear mechanism 234 attached thereto, much like the arrangement in instrument 100. The coupling member 228 is partially disposed within the cavity 230 of the handpiece 202. The gear mechanism 234 is disposed within a slot 236 that is in communication with the cavity 230. The slot 236 opens through part of the handpiece 202, as will be explained in further detail below.

The coupling member 228 further includes an extension element 239 that extends proximally from the gear mechanism 234. A hub element 235 is received within the extension element 239 so as to fix the hub element 235 to the coupling member 228. The proximal end 232 of the central wire 212 extends into the hub element 235 and is fixed connected thereto. The hub 235 serves to facilitate rotation of center wire 212, as will be explained in further detail below.

Much like cavity 130, cavity 230 formed within the handpiece 102 includes several sections. A first section 230a is configured to receive a hub member 226, such that once hub member 226 is disposed within the first section 230a, hub member 226 may not be easily removed from handpiece 102. Hub member 226 has a similar configuration as hub member 226 of instrument 100. In one exemplary arrangement, at least a portion of the handpiece 202 may be separable from a remaining portion, such that the hub member 226 may be positioned within the first section 230a when the two portions of the handpiece 202 are separated. Once positioned, the handpiece 202 is assembled and fixedly secured together to trap the hub member 226 within the first section 230a. In another exemplary arrangement, the hub member 226 may be made of a compliant material having some memory that may be selectively deformed as hub member 226 is press-fit into the first portion 230a. Once the hub member 226 enters the portion 230a of the cavity, the hub member 226 will return to its original shape, thereby being trapped within the first portion 230a.

Cavity 230 further includes a second portion 230b and a second portion 203c. Second portion 230b joins first portion 203a and third portion 230c. Third portion 230c is sized to receive rotation wheel 206 and is thus larger than second portion 230b. Third portion 230c extends into an extension member 237 that extends outwardly from an outer periphery of handpiece 202.

Rotation wheel 206 is mounted to hub member 226 by a web 240. A channel extends through the hub member 226 and opens into slot 236 in similar fashion as the instrument 100. The inner cannula 208 extends through the hub member 226 and has a proximal end 209 that is fixedly secured within a distal extension element 242 of the coupling member 228. The distal extension element 242 of the coupling member 228 is fixedly connected to the rotation wheel 206. Accordingly, the inner cannula 208 is operatively connected to the rotation wheel 206 such that rotation of the rotation wheel 206 causes the coupling member 228 to rotate, thereby rotating the inner cannula 208. Moreover, because the hub element 235 is fixedly connected to the proximal extension element 239, as the rotation wheel rotates the coupling member 228, the hub element 235 will also rotate. This action causes the center wire 212 to rotate. Further because both the inner cannula 208 and the center wire 212 are both connected to the coupling member 228, the inner cannula 208 and the center wire 212 have a fixed rotational relationship. In other words, the inner cannula 208 and the center wire 212 rotate together.

A distal end of the coupling member 208 is received within the cavity of the hub 226 in a similar manner as that described above in connection with instrument 100. In one exemplary arrangement, the coupling member 208 is configured to selectively slide within the cavity relative to the rotation wheel 206, as will be explained in further detail below.

Hub member 226 and coupling member 228 are positioned within cavity 230 formed within a distal portion of handle 202, as best shown in FIG. 10. A portion of rotation wheel 206 is disposed within the third portion of cavity 230c. A remaining portion of the rotation wheel 206 extends outwardly from a portion of the handpiece 202. First actuation member 204 is operatively engaged to gear mechanism 234.

More specifically, in one exemplary arrangement, the first actuation member 204 is configured as a lever and includes teeth members 244 disposed on a distal end 246 thereof that are configured to engage gear 234 formed on the coupling member 228. The teeth members 244 extend through an opening of the handpiece 202 that is in communication with the slot 236. The gear 234 of the coupling member 228 is disposed within the slot 236.

A depression 247 extends proximally from the slot 236 within the handpiece 202. The depression 247 is configured to receive both the extension member 239 of the coupling member 228, as well as the hub element 235. The extension member 239 is configured to be at least partially disposed within the depression 247 to maintain the coupling member 228 within the slot 236 of the handpiece 202.

First actuation member 204 is pivotally attached to a portion of handle 202 such that it is adjacent to rotation wheel 206. In one exemplary configuration a torsional spring (not shown) is engaged at a pivot point A to bias first actuation member 204 into a ready position, namely a position whereby the proximal end 248 of the first actuation member 204 biased upwardly from an outer surface of the handpiece 202. In another alternative arrangement, a coil spring (not shown) is disposed within the cavity 230 to affect the biasing force on the first actuation member 204. When the first actuation member 204 is activated against the biasing force F created by the spring, inner cannula 208 may be advanced forward. This action causes second jaw member 229 to move toward first jaw member 221 within a slot 250 formed in the cap member 220. More specifically, actuation of the first actuation member 204 will cause coupling member 228 to slide forward within the cavity formed by the web member 240 and rotational wheel 206. Because the proximal end of the inner cannula 208 is fixedly connected to the coupling member 228, as the coupling member 228 moves, inner cannula 208 will also move.

Further, to maintain the opposing gripping surface orientation of the first and second jaw members 221, 229, the distal extension member 242 may be operatively connected to the rotation wheel 206 with a splined connection. In another exemplary arrangement, the distal extension member 242 may be a hexagonal cross-section that cooperates with a mating hexagonal opening formed through the rotation wheel 206. Other cross-sectional shapes with corresponding mating openings are also contemplated. With either of these configurations, the inner cannula 208 and the center wire 212 will be rotationally fixed with the rotation wheel 206 such that as rotation wheel 206 rotates, center wire 212 and inner cannula 208 will also rotate. However, the splined connection or mating configuration will enable inner cannula 208 to slide axially, independent of rotation wheel 206.

As the first actuation member 204 is depressed, the inner cannula 208 will traverse the slot 250 formed in the cap member 220, causing the second jaw member 229 to move toward the first jaw member 221, and in particular the gripping surface 233 to more toward gripping surface 223. Any tissue or vessels that are positioned between the first and second jaw members 221, 229 as inner cannula 208 is actuated, will be gripped. Continued depression of first actuation member 204 will maintain the second jaw member 229 against the first jaw member 221.

Because the first and second actuation members 204, 206 are positioned adjacent one another, a user may easily rotate inner cannula 208 and center wire 212 to reposition the distal end of the instrument 200, as well as advance (and retract) inner cannula 208 with a single hand and without requiring removal of the surgical instrument 200 from the surgical site. This configuration allows for reduced visibility concerns, and permits the user to select and maintain an optimal site line, without requiring a user to manually rotate the entire instrument to achieve a desired surgical technique. Further, because the first and second actuation members may be easily activated with a single hand, the second hand is free to handle other surgical instruments that may be necessary during a given procedure.

Figure 12:
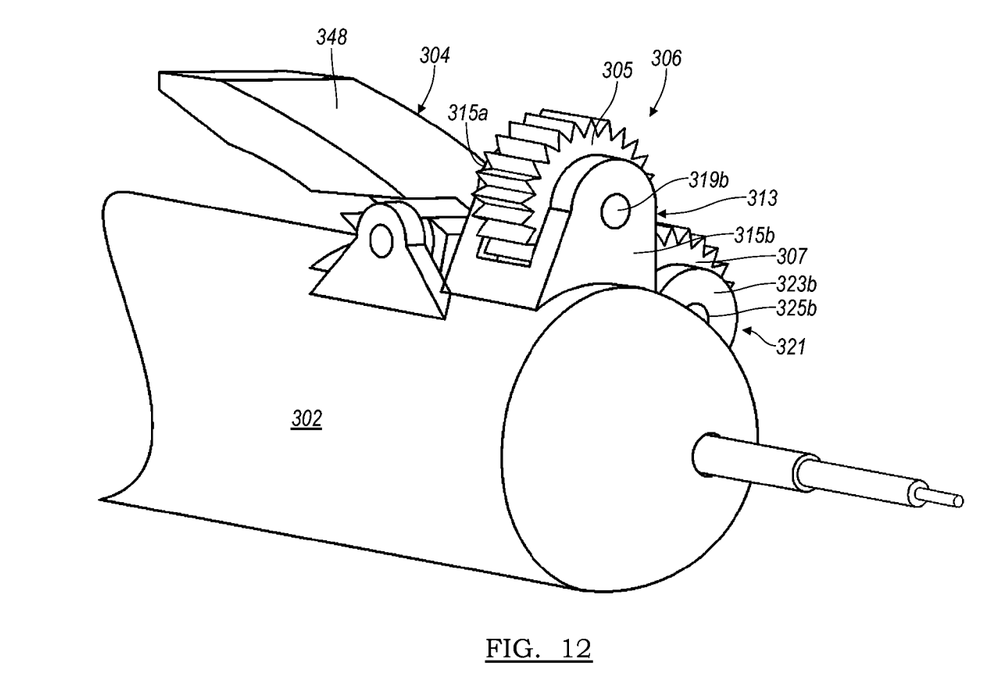
FIG. 12 is a perspective view of a distal end of an alternative arrangement for a surgical device.
Figure 13:
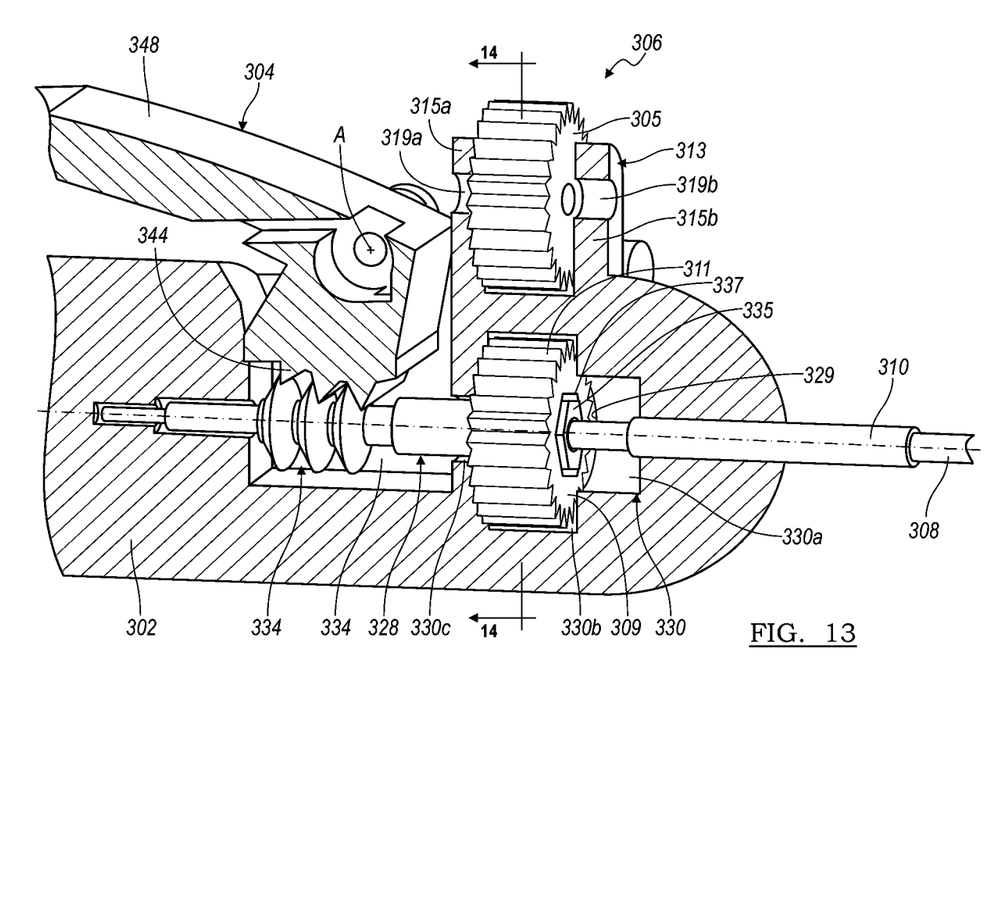
FIG. 13 is a cross-sectional view of the surgical device of FIG. 12.
Figure 14:
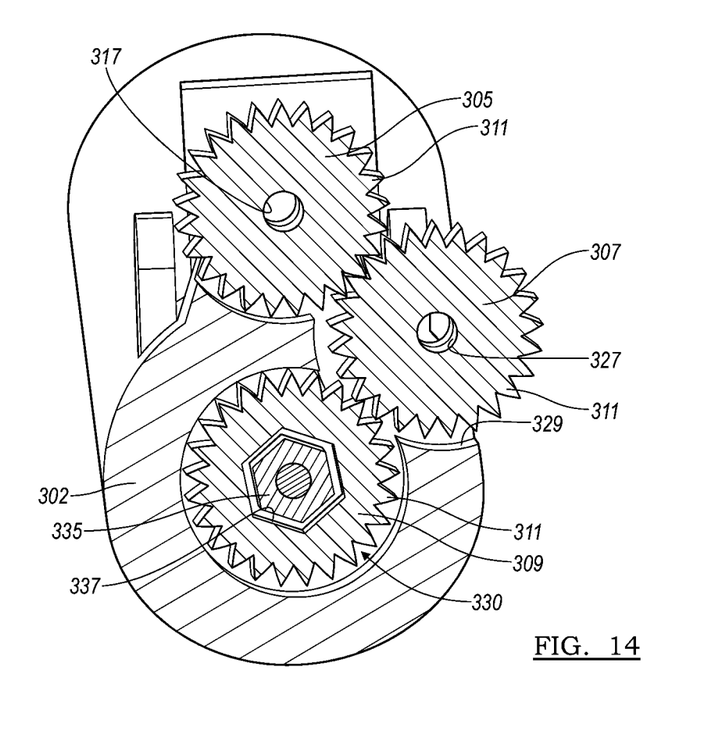
FIG. 14 is a cross-section view of the surgical device of FIG. 12 taken along lines 14-14 in FIG. 13.

An alternative arrangement of a second actuation mechanism 306 that may be utilized with either of microsurgical instruments 100 or 200 is shown in FIGS. 12-14. The second actuation mechanism 306 replaces the rotation wheel 106 and 206 found in instruments 100 and 200.

Second actuation mechanism 306 comprises a first gear wheel 305, a second gear wheel 307 and a third gear wheel 309. Each of the respective gear wheels 305, 307, and 309 include a plurality of gear teeth 311 disposed about their respective peripheries. The gear teeth 311 of each of the respective gear wheels 305, 307 and 309 are configured to mesh together in an operative fashion. All of the gear wheels 305, 307, and 309 are also mounted for rotational movement, as will be discussed in further detail below.

The handpiece 302, to which the gear wheels 305, 307, and 309 are operatively mounted, includes a first mounting yoke 313 that is positioned adjacent the first actuation mechanism 304. The first mounting yoke 313 extends outwardly from an outer periphery of the handpiece 302, as best seen in FIGS. 12-13. The first mounting yoke 313 includes first and second wall members 315a, 315b that are arranged in an opposing manner so as to define a channel therebetween. Each of the wall members 315a, 315b includes an aligned opening 319a, 319b into which a rod member (not shown may be inserted. In one exemplary arrangement, the first mounting yoke 313 may be integrally formed with handpiece 302. Alternatively, the first mounting yoke 313 may be separately secured to the handpiece 302. The first gear wheel 305 is positioned in the channel between the first and second wall members 315a, 315b. The rod member is inserted within the openings 319a, 319b, as well as through an opening 317 (best seen in FIG. 14) formed through the first gear wheel 305. The first gear wheel 305 is configured to be freely rotatable about the rod member.

The second gear wheel 307 is arranged along a common plane 14-14 with first and third gear wheels 305 and 309. The second gear wheel 307 is also mounted on a second mounting yoke 321. Second mounting yoke 321 is constructed in a similar fashion as the first mounting yoke 313 and includes first and second wall members (only second wall member 323b visible) that are arranged in an opposing manner with a channel therebetween. The second yoke member 321 extends radially outwardly from an outer periphery of the handpiece 302. The second gear wheel 307 is positioned with the second yoke 321 and a rod is inserted through aligned openings 325b and an opening 327 of the second gear wheel 307.

As may be best seen in FIG. 14, an inwardly extending groove 329 is formed in the handpiece 302. The groove 329 is in communication with a cavity 330 formed within the handpiece 302 into which the third gear wheel 309 is disposed. The groove 329 serves to position the second gear wheel 307 partially in the handpiece 302 and in meshing engagement with the first and third gear wheels 305 and 309.

Referring to FIG. 13, the handpiece 302 includes a cavity 330. Cavity 330 includes first, second and third cavity portions 330a, 330b, 330c. The second cavity portion 330b is positioned between the first and third cavity portion 330a, 330c and has a length that is larger than the first and third cavity portions 330a, 330c. The third gear wheel 309 is positioned within the second cavity portion 330b. The second cavity portion 330b is in communication with the groove 329. The third cavity portion 330c is in communication with a slot 334 into which a coupling member 328 is positioned. The slot 334 has an opening through the handpiece 302 in a similar fashion as that previously described in connection with instruments 100/200.

The coupling member 328 is similar to those described above in connection with instruments 100/200. More specifically, the coupling member 328 includes a gear mechanism 334, as well as a distal end that includes an engagement section 335. In the exemplary arrangement shown, the engagement section 335 is configured with a hexagonal shape that matingly engages a corresponding opening 337 formed in the third gear wheel 309. With this arrangement, coupling member 328 is able to slide axially within the third gear wheel 309. However, because the engagement section 335 is disposed within the third gear wheel 309, when the third gear wheel 309 rotates, the coupling member 328 will also rotate. The coupling member 328 has an inner cannula 308 that is fixedly mounted to the coupling member 328 in the manner described above in connection with instruments 100/200.

The first actuation member 304 includes teeth members 344 that operatively engage with gear mechanism 334 of the coupling member 328. The first actuation member 304 is pivotally attached to a portion of handpiece 304 such that it is adjacent to the second actuation member 306. In one exemplary configuration a torsional spring (not shown) is engaged at a pivot point A to bias first actuation member 304 into a ready position, namely a position whereby the proximal end 348 of the first actuation member 304 is biased upwardly from an outer surface of the handpiece 302. Further, as an alternative arrangement, a coil spring (not shown) may be disposed within the cavity 320 to bias the first actuation member 304. When the first actuation member 304 is activated against a biasing force created by the spring, the interaction between the teeth members 344 and the gear mechanism 334 cause the coupling member 328 to move forward. Because the inner cannula 308 is fixedly mounted to the coupling member 328, the inner cannula 308 is also moved forward.

Even while advancing the inner cannula 308 by actuating the first actuation member 304, it is possible to selectively rotate the inner cannula 308, as well. More specifically, while one finger is depressing the first actuation member 304, a second finger may be used to selectively rotate the first gear wheel 305. This action will cause the second gear wheel 307 to rotate, due to the intermeshed teeth 311 of the first and second gear wheels 305 and 307, respectively. Once the second gear wheel 307 rotates, the third gear wheel 309 will rotate due to the intermeshing of the teeth 311 of the second and third gear wheels 307, 309. Because the engagement section 335 of the coupling member 328 is disposed within the third gear 309, rotation of the third gear wheel 309 causes the coupling member 328 to rotate. Moreover, because the inner cannula 308 is fixedly connected to the coupling member 328, rotation of the coupling member 328 causes the inner cannula 308 to also rotate.

Figure 15:
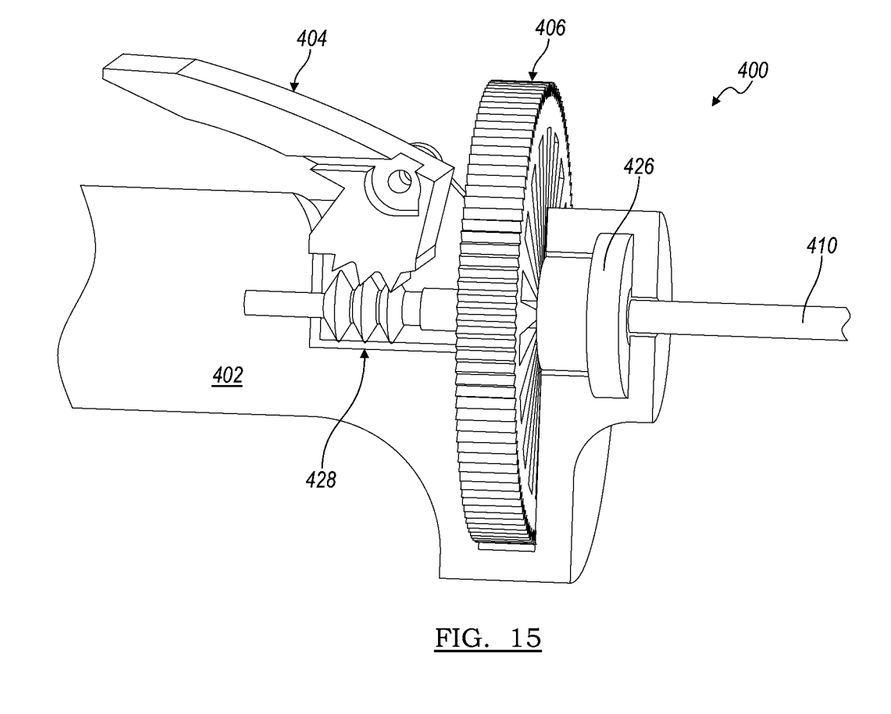
FIG. 15 is a partial cross-sectional view of an alternative microsurgical instrument.

FIG. 15 illustrates a further embodiment of a microsurgical instrument 400. Instrument 400 has basically the same structure as has been described above in connection with instruments 100/200. More specifically, instrument 400 includes a handpiece 402 to which inner and outer cannulas 408, 410, respectively are operatively connected. A coupling member 428 is disposed within the handpiece 402, as is a hub 426. The inner cannula 408a (shown in FIGS. 16-17), 408b (shown in FIGS. 18 and 20) has a proximal end that is fixed to the coupling member 428 in a similar manner as has already been described in connection with instruments 100/200. The outer cannula 410 is fixed to the hub 426 such that the outer cannula 410 may rotate, but not translate. Further, because hub is operatively connected to the coupling member 428, the outer cannula 410 is rotationally fixed with the inner cannula 408.

Figure 16:
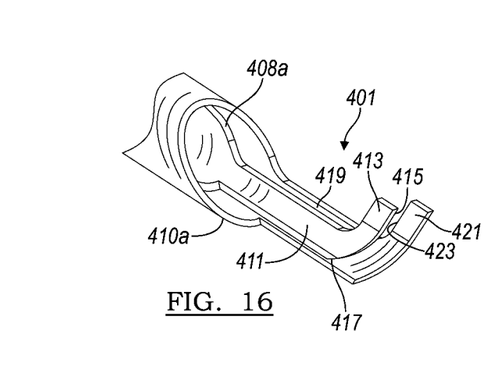
FIG. 16 is a perspective view of a distal end of the microsurgical instrument of FIG. 15.
Figure 17:
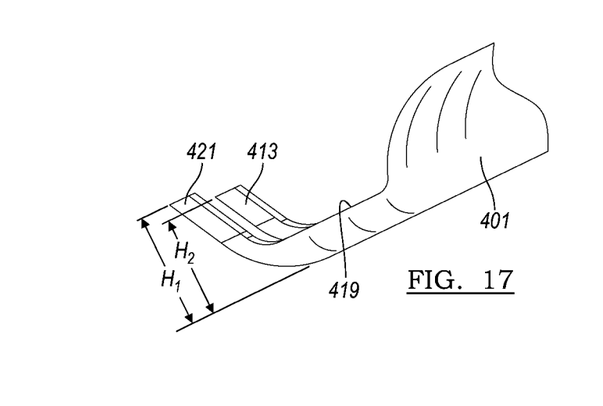
FIG. 17 is a further perspective view of the distal end of the microsurgical instrument of FIG. 15.

Referring to FIGS. 16-17 on exemplary arrangement of a distal end 401 of instrument 400 will now be described. Inner cannula 408a is disposed within outer cannula 410a. Inner cannula 408a may be generally hollow, as depicted, or formed as a solid piece through most of its length. As may be seen in FIG. 16, a portion of a distal end of the inner cannula 408a is removed, leaving a land member 411. Connected to a distal end of the land member 411 is a toe portion 413. Toe portion 413 comprises a portion of the side wall of the inner cannula 408a and is disposed on one side of the land member 411. A distal edge 415 may be sharpened if the instrument is desired to be used as a cutting device. A bottom edge 417 of the distal end of the inner cannula 408a may be beveled to provide for effective sliding relationship between the inner cannula 408a and the outer cannula 410a. The wall of the inner cannula 408a adjacent the land member 411 may be beveled toward the land member 411 to provide for improved line of sight.

The outer cannula 410a is generally hollow, as well. A portion of the distal end of the outer cannula 410a is also removed, leaving a land member 419. Connected to a distal end of the land member 419 is a toe portion 421. Toe portion 421 comprises a portion of the side wall of the outer cannula 410a and is disposed on the same side of the land member 419 of the outer cannula 410a as the toe portion 413 of the inner cannula 408a. A proximal edge 423 may be sharpened if the instrument is desired to be used as a cutting device. The wall of the outer cannula 410a adjacent the land member 419 may be beveled toward the land member 419 to provide for improved line of sight of the distal end 401 of the instrument. In one exemplary arrangement, the toe portion 421 of the outer cannula 410a may be provided with a height $H_1$ that is longer than the height $H_2$ of the toe portion 413 of the inner cannula 408a. This will also serve to provide an improved line of sight during a procedure, as well as allow for effective manipulation of tissue.

In operation, the outer cannula 410a is fixed against axial movement, but may rotate in response to activation of the second actuation member 406 (along with inner cannula 408a). The inner cannula 408a may be selectively advanced to bring the respective toe portions 413, 421 of the inner and outer cannula 408a, 410a together. More specifically, actuation of the first actuation member 404 will cause the coupling member 428 to advance distally. As the coupling member 482 carries the inner cannula 408a, the toe portion 413 of the inner cannula 408a will move toward the toe portion 421 of the outer cannula 410a. If the edges 415 and 423 are configured as sharpened edges, the actuation of the first actuation member 408a will achieve a cutting action. If the edges 415 and 423 are not configured with a sharpened edge, the interaction of the inner and outer cannulas 408a, 410a will operate as a grasping device.

Figure 18:
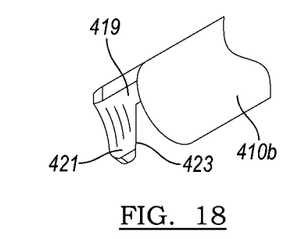
FIG. 18 is a perspective view of an outer cannula used with an alternative distal end of a microsurgical instrument of FIG. 15.
Figure 19:
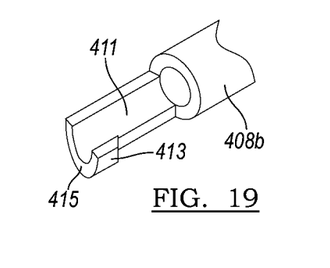
FIG. 19 is a perspective view of an inner cannula used with the outer cannula of FIG. 18.

A further alternative arrangement of a distal end 401 of instrument 400 will now be described in connection with FIGS. 18-20. Inner cannula 408b is configured to be disposed within outer cannula 410b. Inner cannula 408b may be generally hollow, as depicted, or formed as a solid piece through most of its length. As may be seen in FIG. 18, a portion of a distal end of the inner cannula 408b is removed, leaving a land member 411. Connected to a distal end of the land member 411 is a toe portion 413. Toe portion 413 comprises a portion of the side wall of the inner cannula 408b and is disposed on one side of the land member 411. A distal edge 415 may be sharpened if the instrument is desired to be used as a cutting device. While not shown, it is understood that the wall of the inner cannula 408b adjacent the land member 411 may be beveled toward the land member 411 to provide for improved line of sight.

The outer cannula 410b is generally hollow, as well. A portion of the distal end of the outer cannula 410b is also removed, leaving a land member 419. Connected to a distal end of the land member 419 is a toe portion 421. Toe portion 421 comprises a portion of the side wall of the outer cannula 410b and is disposed on the same side of the land member 419 of the outer cannula 410b as the toe portion 413 of the inner cannula 408b. A proximal edge 423 may be sharpened if the instrument is desired to be used as a cutting device. The wall of the outer cannula 410b adjacent the land member 419 may be beveled toward the land member 419 to provide for improved line of sight of the distal end 401 of the instrument. In one exemplary arrangement, the toe portion 421 of the outer cannula 410b may be provided with a height that is longer than the height of the toe portion 413 of the inner cannula 408b. This will also serve to provide an improved line of sight during a procedure, as well as allow for effective manipulation of tissue.

In operation, the outer cannula 410b is fixed against axial movement, but may rotate in response to activation of the second actuation member 406 (along with inner cannula 408b). The inner cannula 408b may be selectively advanced to bring the respective toe portions 413, 421 of the inner and outer cannula 408a, 410a together, as is shown in FIG. 20. More specifically, actuation of the first actuation member 404 will cause the coupling member 428 to advance distally. As the coupling member 482 carries the inner cannula 408b, the toe portion 413 of the inner cannula 408b will move toward the toe portion 421 of the outer cannula 410b, as the inner cannula 408b is nested within the outer cannula 410b. If the edges 415 and 423 are configured as sharpened edges, the actuation of the first actuation member 408a will achieve a cutting action. If the edges 415 and 423 are not configured with a sharpened edge, the interaction of the inner and outer cannulas 408a, 410a will operate as a grasping device.

Figure 20:
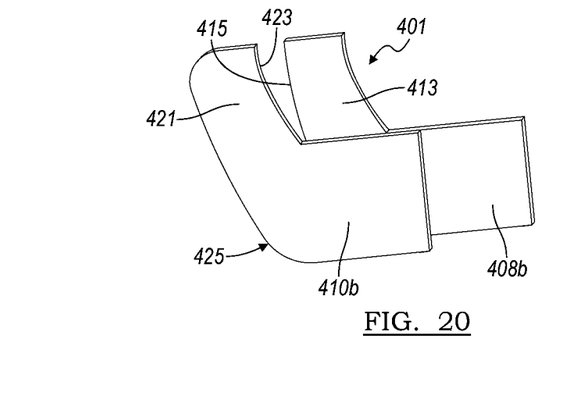
FIG. 20 is an enlarged elevational view of a distal end of a microsurgical device that illustrates the interaction of the inner and outer cannulas of FIGS. 18 and 19.

Referring to FIG. 20, in one exemplary arrangement, a distal edge 425 may be rounded to remove a sharp corner, thereby lessening potential tissue damage during operation. Further the distal edge 415 of the inner cannula 408b may be configured to be disposed at a more vertical angle than a coincident point of the outer cannula 410b. This configuration permits a heavy bias to be introduced to the toe portions 413, 421 to cause the toe portions 413, 421 to rub together without getting caught on each other during repeated actuations.

The land members 411/419 and toe portions 413/421 of the inner and outer cannulas may be constructed using a series of planar wire EDM cuts. In one exemplary arrangement, the wire used for the inner and outer cannulas may be subjected to a first cut operation and then the tubing is rotated 90 degrees for a second cut to achieve a configuration that may be flattened out into the desired final toe portion shape.

It will be appreciated that the surgical instrument and methods described herein have broad applications. The foregoing embodiments were chosen and described in order to illustrate principles of the methods and apparatuses as well as some practical applications. The preceding description enables others skilled in the art to utilize methods and apparatuses in various embodiments and with various modifications as are suited to the particular use contemplated. In accordance with the provisions of the patent statutes, the principles and modes of operation of this disclosure have been explained and illustrated in exemplary embodiments.

It is intended that the scope of the present methods and apparatuses be defined by the following claims. However, it must be understood that this disclosure may be practiced otherwise than is specifically explained and illustrated without departing from its spirit or scope. It should be understood by those skilled in the art that various alternatives to the embodiments described herein may be employed in practicing the claims without departing from the spirit and scope as defined in the following claims. The scope of the disclosure should be determined, not with reference to the above description, but should instead be determined with reference to the appended claims, along with the full scope of equivalents to which such claims are entitled. It is anticipated and intended that future developments will occur in the arts discussed herein, and that the disclosed systems and methods will be incorporated into such future examples. Furthermore, all terms used in the claims are intended to be given their broadest reasonable constructions and their ordinary meanings as understood by those skilled in the art unless an explicit indication to the contrary is made herein. In particular, use of the singular articles such as "a," "the," "said," etc. should be read to recite one or more of the indicated elements unless a claim recites an explicit limitation to the contrary. It is intended that the following claims define the scope of the invention and that the method and apparatus within the scope of these claims and their equivalents be covered thereby. In sum, it should be understood that the invention is capable of modification and variation and is limited only by the following claims.

What is claimed is:

1. A surgical instrument, comprising:
   a housing;
   a lever to impart a reciprocating action to a portion of the instrument, the lever mounted to the housing;
   a wheel arranged adjacent to the lever and mounted within the housing;
   a first cannula fixedly connected to the wheel, such that the first cannula is rotationally fixed with the wheel and the first cannula is selectively rotatable with respect to the housing in response to actuation of the wheel,
   a wire member disposed within the first cannula and configured to rotate with the first cannula; and
   a second cannula non-rotatably fixed to the housing.

2. The surgical instrument of claim 1, wherein the first cannula further comprises a cut block disposed at a distal end thereof.

3. The surgical instrument of claim 1, wherein the wire member includes a cutting edge at a distal end thereof.

4. The surgical instrument of claim 1, wherein the first cannula includes a plurality of relief cut-outs, whereby the relief cut-outs allow the first cannula to be bent to a desired shape, while maintaining columnar strength.

5. The surgical instrument of claim 4, wherein the wire includes a plurality of relief cut-outs, whereby the relief cut-outs allow the wire to be bent to a desired shape, while maintaining columnar strength.

6. The surgical instrument of claim 1, wherein the first cannula further comprises an opening positioned at a distal end thereof, and wherein the wire member is operatively connected to the lever to selectively reciprocate the wire member across the opening upon actuation of the first actuation member.

7. The surgical instrument of claim 1, wherein the wheel is fixed to a hub member, whereby the first cannula is fixed to a portion of the hub member such that actuation of the wheel causes the first cannula to rotate.

8. The surgical instrument of claim 7, wherein a coupling member includes a keyed distal end that engages a portion of the rotation wheel such that as the rotation wheel rotates, the coupling member rotates, and wherein the keyed distal end is configured to axially slide within the rotation wheel.

9. The surgical instrument of claim 8, whereby the wire member is fixedly connected to the coupling member such that the first cannula and the wire member are rotationally fixed with respect to one another.

10. The surgical instrument of claim 1, further comprising a cap member, wherein the cap member is fixedly connected to a distal end of the wire member and wherein the cap member carries a first jaw member; and wherein a distal end of the first cannula carries a second jaw member, and wherein the first and second jaw members are configured to come together.

11. The surgical instrument of claim 10, wherein the lever that includes teeth members that are configured to engage teeth on a gear mechanism that is carried by a coupling member, whereby the first cannula is fixed to the coupling member such that as the lever is actuated, the first cannula will translate, thereby moving the second jaw member.

12. The surgical instrument of claim 11, further comprising a hub element disposed proximally of coupling member, wherein the hub element is configured for rotational movement and wherein the wire member is fixedly connected to the hub element.

13. The surgical instrument of claim 1, wherein the second cannula is disposed over the first cannula.

14. A surgical instrument, comprising:
a housing;
a first actuation member comprising a lever member that includes teeth members that are configured to engage teeth on a gear mechanism that is carried by a coupling member, the first actuation member imparting a reciprocating action to a portion of the instrument;
a second actuation member arranged adjacent the first actuation member to impart a rotational action to a portion of the instrument;
a first cannula operatively connected to the second actuation member, such that the first cannula is configured for rotational movement with respect to the housing in response to actuation of the second actuation member, and
a wire member disposed within the first cannula and fixed to the coupling member, wherein the wire member is configured to rotate with the first cannula.

15. A surgical instrument, comprising:
a housing;
a first actuation member to impart a reciprocating action to a portion of the instrument;
a second actuation member arranged adjacent the first actuation member to impart a rotational action to a portion of the instrument;
a first cannula operatively connected to the second actuation member, such that the first cannula is configured for rotational movement with respect to the housing in response to actuation of the second actuation member, wherein a distal end of the first cannula has a narrow portion that is narrower than a greatest diameter of the first cannula; and
a wire member disposed within the first cannula and configured to rotate with the first cannula.

16. The surgical instrument of claim 15, wherein the narrower portion further comprises opposing lateral surfaces positioned inboard of the greatest diameter of the first cannula.

* * * * *